(12) United States Patent
Willett et al.

(10) Patent No.: US 11,774,424 B2
(45) Date of Patent: Oct. 3, 2023

(54) INTEGRATED SENSOR

(71) Applicant: Honeywell International Inc., Charlotte, NC (US)

(72) Inventors: Martin Willett, Waterlooville (GB); Keith Pratt, Portsmouth (GB)

(73) Assignee: Honeywell International Inc., Charlotte, NC (US)

( * ) Notice: Subject to any disclaimer, the term of this patent is extended or adjusted under 35 U.S.C. 154(b) by 112 days.

(21) Appl. No.: 17/209,841

(22) Filed: Mar. 23, 2021

(65) Prior Publication Data

US 2022/0308029 A1  Sep. 29, 2022

(51) Int. Cl.
*G01N 33/00* (2006.01)
*G01N 21/3504* (2014.01)
*G01N 27/12* (2006.01)
*H05K 1/18* (2006.01)

(52) U.S. Cl.
CPC ....... *G01N 33/005* (2013.01); *G01N 21/3504* (2013.01); *G01N 27/122* (2013.01); *H05K 1/181* (2013.01); *H05K 2201/10151* (2013.01)

(58) Field of Classification Search
CPC ............ G01N 33/005; G01N 21/3504; G01N 27/122; H05K 1/181; H05K 2201/10151
USPC ........................................................ 73/31.06
See application file for complete search history.

(56) References Cited

U.S. PATENT DOCUMENTS

| 4,507,558 A | * | 3/1985 | Bonne .................. G01N 21/031 |
| | | | 250/343 |
| 2005/0259262 A1 | * | 11/2005 | Fischer ............. G01N 21/3504 |
| | | | 356/440 |
| 2008/0116378 A1 | | 5/2008 | Frodl et al. |
| 2022/0308029 A1 | * | 9/2022 | Willett ................. G01N 21/031 |

FOREIGN PATENT DOCUMENTS

| CN | 108931504 A | * | 12/2018 | ............ G01N 21/61 |
| CN | 212159555 U | * | 12/2020 | |
| CN | 216350333 U | * | 4/2022 | |
| EP | 1695066 | * | 8/2006 | ............ G01N 21/03 |
| EP | 4063832 A1 | * | 9/2022 | ........ G01N 21/3504 |
| KR | 20170032735 A | * | 9/2015 | ............ G01N 33/00 |
| KR | 10-2017-0032735 A | | 3/2017 | |
| KR | 20170032735 A | * | 3/2017 | ........ G01N 21/3504 |
| WO | WO-2005057188 A1 | * | 6/2005 | .......... G01N 2/0303 |
| WO | WO-2019228407 A1 | * | 12/2019 | ............ G01N 21/61 |

OTHER PUBLICATIONS

European search report dated Jul. 27, 2022 for EP Application No. 22160737.

\* cited by examiner

*Primary Examiner* — Stephanie E Bloss
*Assistant Examiner* — Kevin C Butler
(74) *Attorney, Agent, or Firm* — Alston & Bird LLP

(57) ABSTRACT

An integrated sensor for detecting gases present in an environment is provided. The integrated sensor comprises a first gas sensor and a second gas sensor. The first gas sensor is configured to measure a first gas and the second gas sensor is configured to measure a second gas. The first gas is (Continued)

different from the second gas. The first gas sensor is an optical sensor and defines an optical cavity. The second gas sensor is disposed within the optical cavity of the first gas sensor.

20 Claims, 8 Drawing Sheets

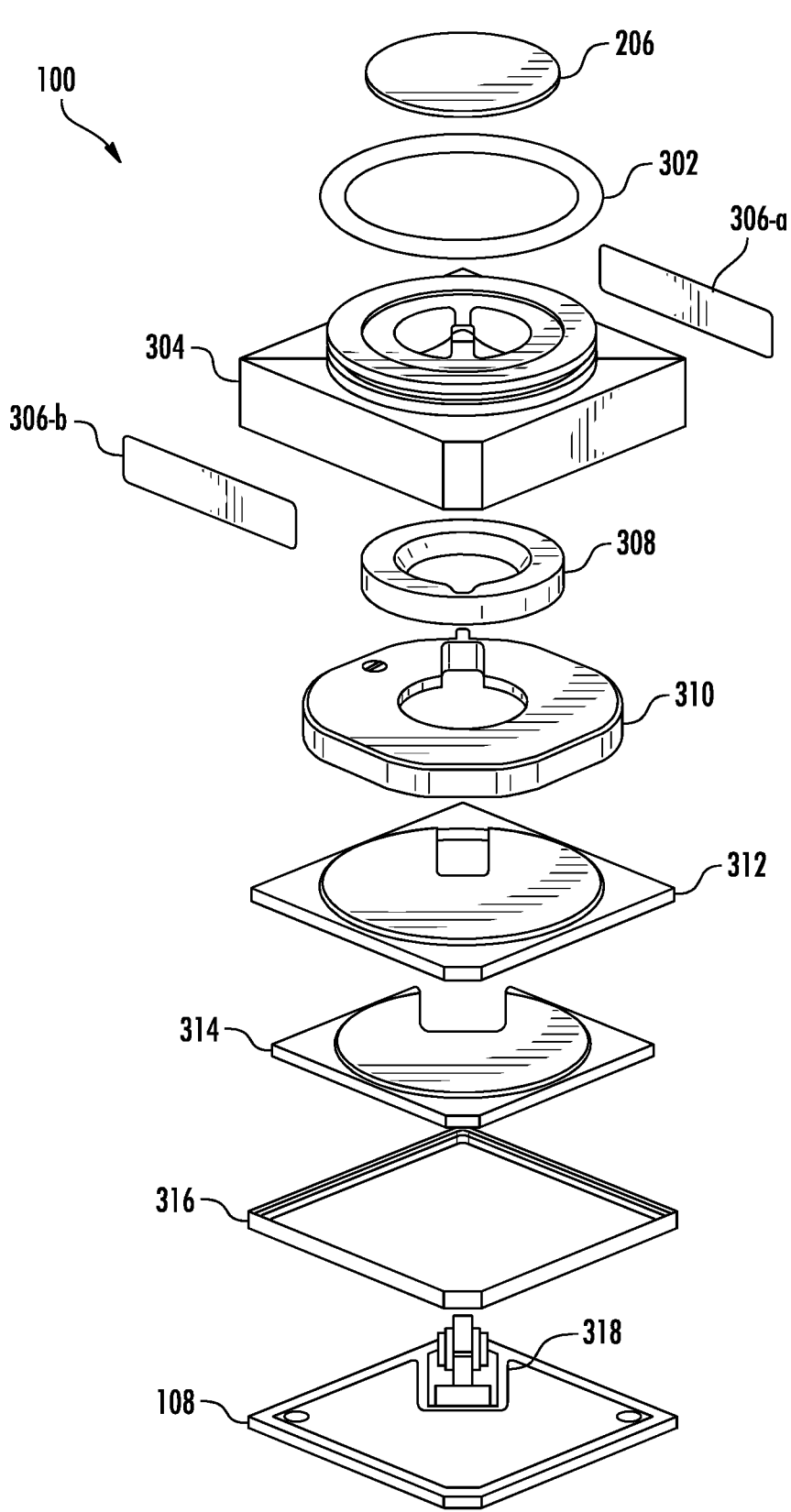

INTEGRATED SENSOR

TECHNOLOGICAL FIELD

Example embodiments of the present disclosure relate generally to an integrated sensor, and more particularly, to a Non-Dispersive Infrared (NDIR) sensor integrated with a hydrogen sensor.

BACKGROUND

Non-dispersive infrared (NDIR) sensors typically comprise an IR source, a sample chamber containing a gas sample, and a detector, disposed in an optical cavity of the NDIR sensor. The detector may comprise optical bandpass filters depending on a target gas to be detected. Radiations transmitted by the IR source travel within a region of the optical cavity to be received by the detector. The radiations of specific wavelength may be absorbed by gas molecules of the target gas. A difference between an amount of radiations transmitted by the IR source and the amount of IR radiation received by the detector is measured and is indicative of the IR radiation being absorbed by the gas molecules in the air inside the sample chamber.

Generally, NDIR sensors are preferred over traditional catalytic devices due to reductions in power consumption by the NDIR sensors and reliability and accuracy of readings. Additionally, the NDIR sensors are low cost and provide a stable long-term operation.

BRIEF SUMMARY

The illustrative embodiments of the present disclosure relate to an integrated sensor for detecting gases present in an environment. The integrated sensor comprises a first gas sensor and a second gas sensor. The first gas sensor is configured to measure a first gas and the second gas sensor is configured to measure a second gas. The first gas is different from the second gas. The first gas sensor is an optical sensor and defines an optical cavity. The second gas sensor is disposed within the optical cavity of the first gas sensor.

In an example embodiment, the optical cavity of the first gas sensor comprises a region having a low optical intensity of radiations when the first gas sensor is operated to measure the first gas.

In an example embodiment, the first gas sensor comprises a Printed Circuit Board Assembly (PCBA) placed within the region of the optical cavity having low optical intensity, and the second gas sensor mounted on the PCBA.

In an example embodiment, the second gas sensor is a hydrogen gas sensor.

In an example embodiment, the hydrogen gas sensor is at least one of a small solid-state electrochemical sensor or a Metal Oxide Semiconductor (MOS) sensor.

In an example embodiment, the first gas sensor is a Non-Dispersive Infrared (NDIR) sensor.

In an example embodiment, the integrated sensor comprises a cylindrical ring in the optical cavity and two reflective plates, wherein the two reflective plates are arranged on opposite sides of the cylindrical ring.

In an example embodiment, the integrated sensor comprises a housing and a turret, wherein the turret is disposed on a top portion of the housing.

In some embodiments, the turret comprises a dust cover disposed on a top portion of the turret.

In an example embodiment, the turret further comprises an elastomer seal positioned beneath the dust cover.

In some embodiments, a Non-Dispersive Infrared (NDIR) for measuring a first gas and defining an optical cavity, comprises a printed circuit board assembly (PCBA) disposed within the optical cavity of the NDIR sensor. The PCBA comprises a gas sensor mounted on the PCBA, the gas sensor configured to measure a second gas, wherein the first gas is different from the second gas.

In an example embodiment, the gas sensor is a hydrogen gas sensor.

In an example embodiment, the hydrogen gas sensor is at least one of a small solid-state electrochemical sensor or a Metal Oxide Semiconductor (MOS) sensor.

In some embodiments, the optical cavity comprises a region having a low optical intensity of radiations when the NDIR sensor is operated to measure the first gas.

In an example embodiment, the PCBA is disposed within the region of the optical cavity having low optical intensity.

In an example embodiment, the optical cavity is coated with gold.

In an example embodiment, the NDIR sensor comprising a cylindrical ring in the optical cavity and two reflective plates, wherein the two reflective plates are arranged on opposite sides of the cylindrical ring.

In an example embodiment, the NDIR sensor comprises a housing and a turret, wherein the turret is disposed on a top portion of the housing.

In some embodiments, the turret comprises a dust cover disposed on a top portion of the turret.

In various embodiments, the turret further comprises an elastomer seal positioned beneath the dust cover.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which:

FIG. 3 is an exploded view of an integrated sensor, in accordance with an example embodiment of the present disclosure;

DETAILED DESCRIPTION

Figure 1A:
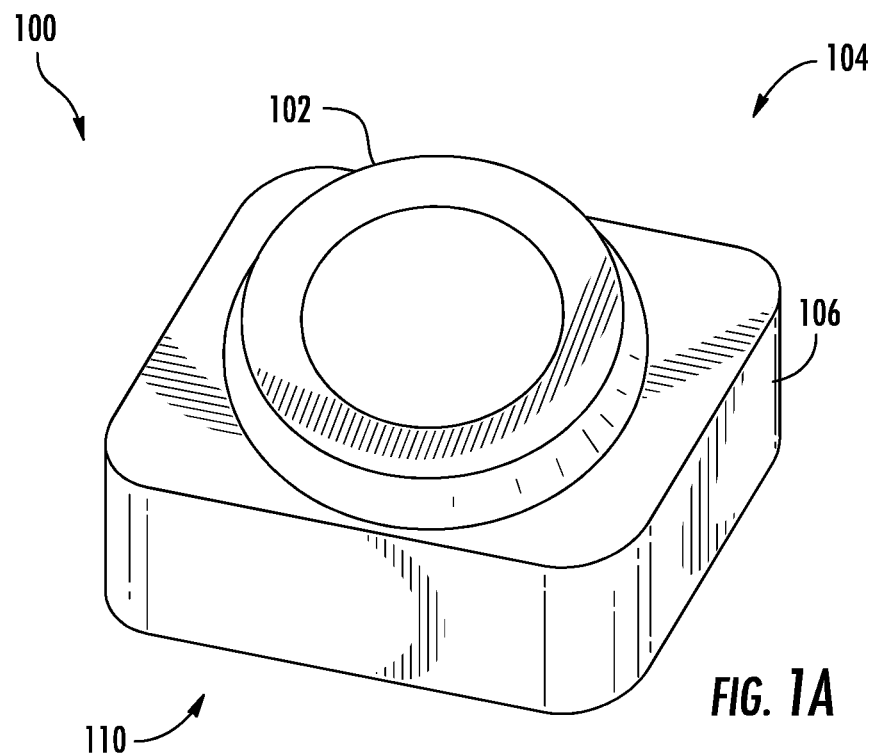
FIGS. 1A-1B illustrate perspective view of an integrated sensor for detecting gases, in accordance with an example embodiment of the present disclosure.

Some embodiments of the present disclosure will now be described more fully hereinafter with reference to the accompanying drawings, in which some, but not all embodiments are shown. Indeed, the disclosure may be embodied in many different forms and should not be construed as limited to the embodiments set forth herein; rather, these embodiments are provided so that this disclosure will satisfy applicable legal requirements. The terms "or" and "optionally" are used herein in both the alternative and conjunctive sense, unless otherwise indicated. The terms "illustrative" and "exemplary" are used to be examples with no indication of quality level. Like numbers refer to like elements throughout.

The components illustrated in the figures represent components that may or may not be present in various example embodiments described herein such that embodiments may include fewer or more components than those shown in the figures while not departing from the scope of the disclosure.

Turning now to the drawings, the detailed description set forth below in connection with the appended drawings is intended as a description of various example configurations and is not intended to represent the only configurations in which the concepts described herein may be practiced. The detailed description includes specific details for the purpose of providing a thorough understanding of various concepts with like numerals denoting like components throughout the several views. However, it will be apparent to those skilled in the art of the present disclosure that these concepts may be practiced without these specific details.

Non-dispersive Infrared (NDIR) sensors are increasingly being used to offer major power consumption reductions over traditional catalytic devices. The NDIR sensors fail to detect hydrogen ($H_2$) which has no infrared signature. Existing sensors require a dedicated external hydrogen sensor to be included in a housing of a primary sensor. Incorporating the hydrogen sensor requires substantial space within a multi-gas sensor. Such sensors consume power and are not immune to poisoning offered by NDIR sensors. Existing hydrogen electrochemical sensors are not readily integrated with miniature IR gas sensors and require careful design to prevent electrolyte leakage. The process of combining these sensors is complex.

Various example embodiments described in the present disclosure relate to an integrated sensor such as a NDIR sensor integrated with a hydrogen sensor for detecting presence of gases in an environment. The integrated sensor comprises a first gas sensor and a second gas sensor. The first gas sensor is, for instance the NDIR sensor, configured to measure a first gas and the second gas sensor, such as hydrogen sensor, is configured to measure a second gas. The first gas is for example methane ($CH_4$). In another example, the first gas is carbon dioxide ($CO_2$) or a similar gas and is different from the second gas, which is hydrogen. The first gas sensor defines an optical cavity within which an IR source or emitter and detector are disposed. The second gas sensor is disposed within the optical cavity of the first gas sensor.

The details regarding components of the integrated sensor and their working is described in detail with reference to subsequent figures and description.

Figure 1B:
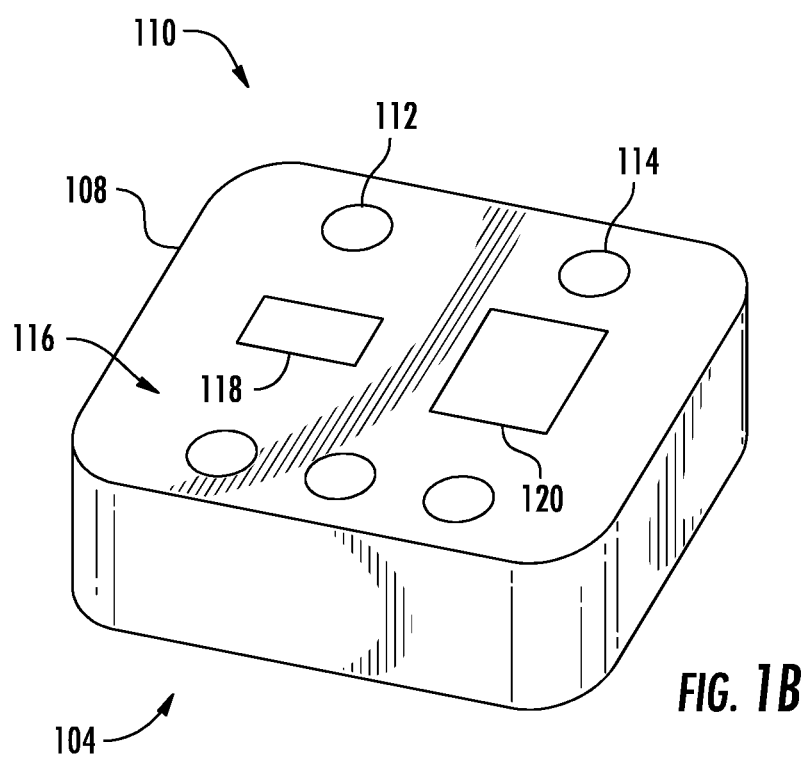

FIGS. 1A-1B illustrates an integrated sensor 100 having a turret 102, in accordance with an example embodiment of the present disclosure. The integrated sensor 100 comprises the turret 102 on a top side 104, an external housing 106, and a printed circuit board assembly (PCBA) 108 on a bottom side 110. As shown, the turret 102 is part of the external housing 106. The turret 102 is an empty space and, in an example, is used for housing a gas filter. The turret 102 comprises an optical cavity. In an example, the optical cavity is coated with gold to increase reflectivity. The PCBA 108 comprises voltage contacts 112 and 114, and other contacts 116 for electrodes or transmitters or receivers. The PCBA 108 also comprises a sensor circuit 118 for the NDIR sensor and a second gas sensor 120 disposed on PCB board. The details of the PCBA 108 and the second gas sensor such as the hydrogen sensor is explained in detail with subsequent figures.

Figure 2A:
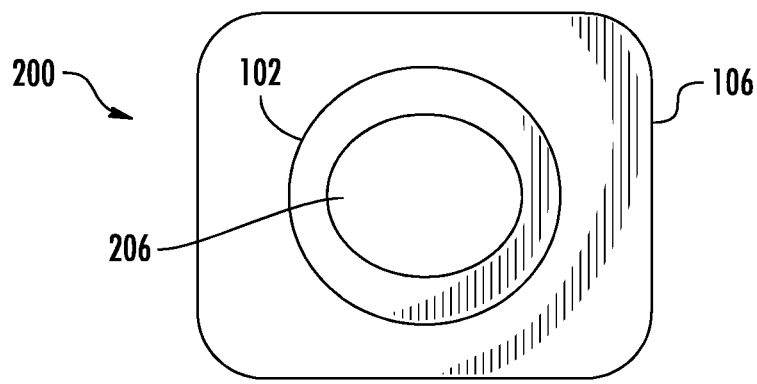
FIGS. 2A-2C illustrate various views of an integrated sensor for detecting multiple gases in accordance with an example embodiment of the present disclosure.
Figure 2B:
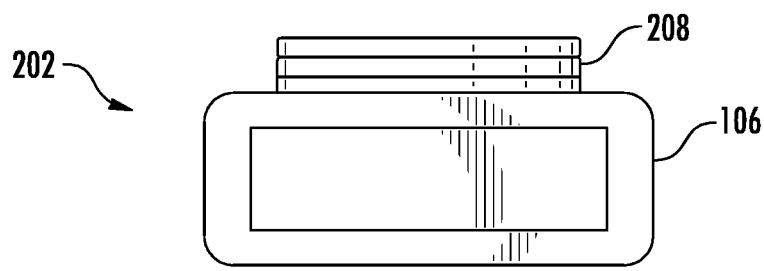
Figure 2C:
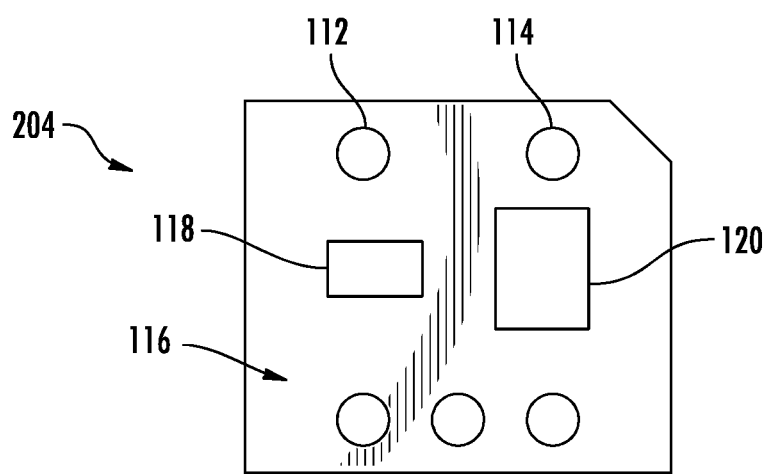

FIGS. 2A-2C illustrate various views of the integrated sensor 100, in accordance with an example embodiment of the present disclosure. FIG. 2A illustrates a top view 200, FIG. 2B illustrates a side view 202 and FIG. 2C illustrates a bottom view 204 of the integrated sensor 100. FIG. 2A illustrate the turret 102 and the external housing 106. The turret 102 comprises a dust cover 206. In an example, the dust cover 206 has a circular shape. The shape of the dust cover 206 varies based on the shape of the external housing 106 and an opening within the external housing 106 in which the dust cover 206 is placed to cover. In an example, the external housing 106 has a length of 10 millimeters (mm), and a diameter of the dust cover 206 is 12.30 mm.

In an example, the turret 102 comprises an elastomer seal 208 as shown in FIG. 2B. The elastomer seal 208 is placed in between the dust cover 206 and a top surface of the external housing 106. In an example embodiment, a length of the turret 102 is in a range of 17.56-17.76 mm, and a length of the dust cover 206 is 17 mm. In an example embodiment, a height of the external housing 106 is in a range from 6.85 mm to 7.15 mm. In another example, a height of the integrated sensor 100 including the dust cover 206 is 10.25 mm.

In an embodiment, the PCBA 108 is disposed within the optical cavity and includes a sensor circuit 118 of the first gas sensor, such as an optical sensor. The sensor circuit 118 is used for determining and measuring gas concentration of a target gas in the environment. In an example, the optical sensor is a Non-dispersive Infrared (NDIR) sensor for measuring a first gas, which is for instance, methane ($CH_4$). In another example, the first gas is carbon dioxide ($CO_2$). The PCBA 108 also includes a second gas sensor 120, such as a hydrogen sensor to detect a second gas, hydrogen. The hydrogen sensor in an example can be one of a small solid-state electrochemical sensor or a Metal Oxide Semiconductor (MOS) sensor. The hydrogen sensor can be any other type of sensor that can be used with the NDIR sensor. In an example, the second gas sensor 120 can be any other gas sensor, for instance, a carbon monoxide (CO) sensor or a Volatile organic compound (VOC) sensor.

FIG. 3 illustrates an exploded view of the integrated sensor 100, in accordance with an example embodiment of the present disclosure. The integrated sensor 100 comprises the dust cover 206, an O-Ring 302, a housing 304 having labels 306-a and 306-b placed on opposite sides of the housing 304. Further, the integrated sensor 100 comprises a stuffing 308, a ring optical 310, a base optical 312, glues 314 and 316 and the PCBA 108. The PCBA 108 comprises a base PCB and a vertical component or a vertical PCB 318.

As shown in FIG. 3, in an assembled state, the vertical component or the vertical PCB 318 passes through openings of the base optical 312, the ring optical 310 and the stuffing 308. The glues 314 and 316 secure the PCBA 108 to the base optical 312. In the assembled state, the PCBA 108 and the vertical PCB 318 are disposed within the optical cavity of the integrated sensor 100. In an example embodiment, the hydrogen sensor is positioned on the PCBA 108. In such an embodiment one or more openings are provided in the base optical 312 and ring optical 310 to provide electrical connection to the hydrogen sensor. In another example embodiment, the hydrogen sensor is disposed on the vertical PCB 318, explained in detail with respect to FIG. 8.

Figure 4A:
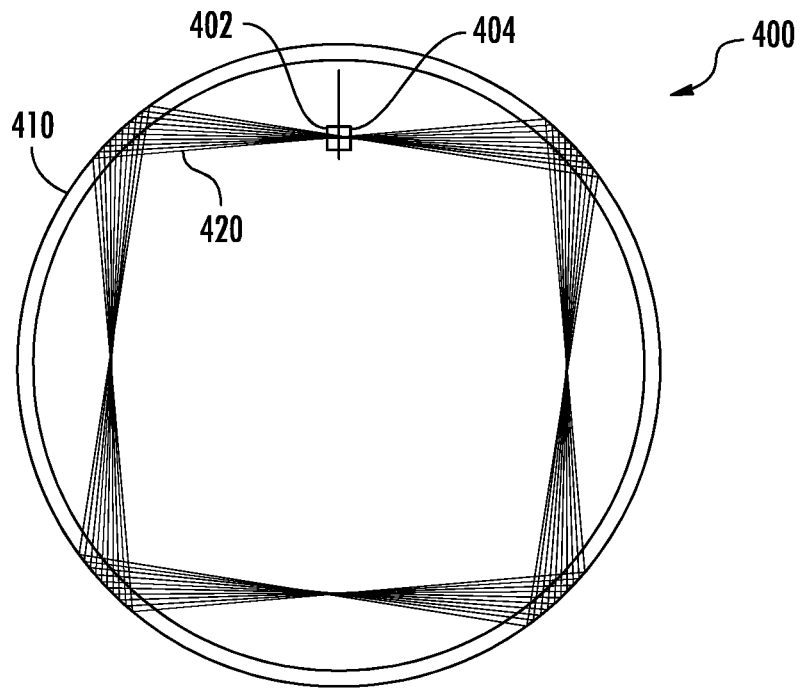
FIGS. 4A-4B illustrates a spheroid ring reflector of an integrated sensor, in accordance with an example embodiment of the present disclosure.
Figure 4B:
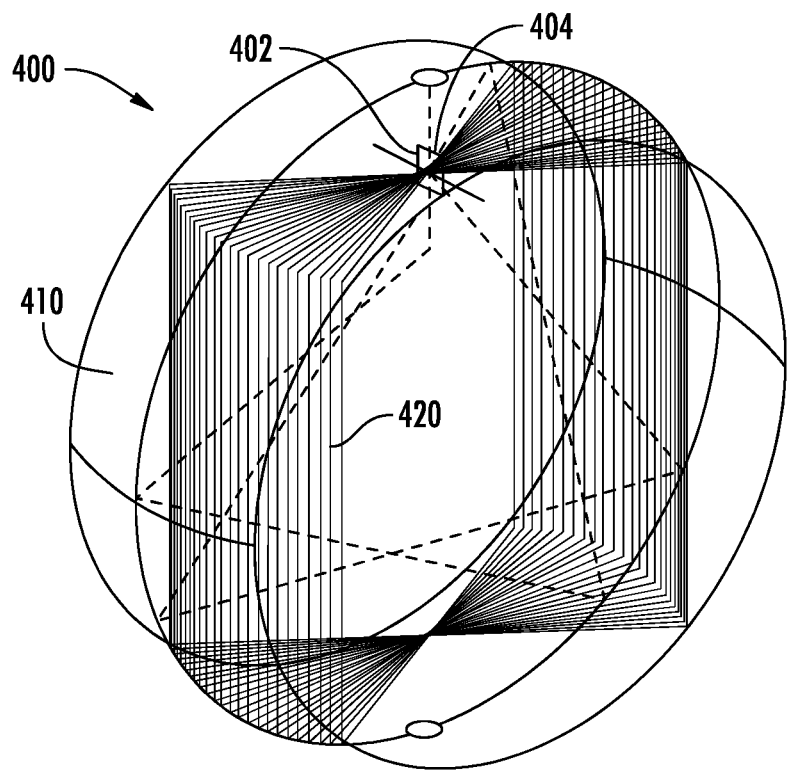

Referring now to FIGS. 4A-4B, an exemplary spheroid ring reflector 400 is shown. The spheroid ring reflector 400 comprises an emitter 402 (or a radiation source) configured to emit radiation, which may for example comprise infrared (IR) radiation and/or a light emitting diode (LED). In some embodiments, the emitter 402 may be modulated. The spheroid ring reflector 400 may also comprise a detector 404 configured to receive the emitted radiation. In some embodiments, the spheroid ring reflector 400 may comprise curved walls 410, wherein a beam path 420 from the emitter 402 may reflect off of the curved walls 410 and be directed toward the detector 404. The curved walls 410 may "contain" the beam path 420 within the spheroid ring reflector 400, allowing for focusing of the beam path 420 toward the detector 404, and preventing continuous expansion of the beam path 420. In the embodiment shown in FIGS. 4A and 4B, the emitter 402 and detector 404 may be oriented back to back. However, other orientations for the emitter 402 and detector 404 may also be used.

In some embodiments, the emitter 402 and detector 404 could possibly be mounted side by side, back to back, opposing sides, or in another orientation. The radiation from the emitter 402 may be directed toward the detector 404 using the spheroid ring reflector 400 itself as well as optionally other reflector elements.

In use, a gas may be passed through the spheroid ring reflector 400 while the radiation is being directed from the emitter 402 toward the detector 404. In some embodiments, the detector 404 may comprise one or more filters for a target wavelength and/or a reference wavelength. In some embodiments, the emitter 402 may comprise one or more filters, and/or a plurality of filters may be used within the spheroid ring reflector 400. The detection of the target wavelength may be correlated to the presence and/or amount of a target gas within the gases that are passed through the spheroid ring reflector 400. As an example, the gases passing through the spheroid ring reflector 400 may comprise flammable gases, hydrocarbons, CO and/or $CO_2$, among other things.

In some embodiments, different methods may be used to fan the beam path 420 from the emitter 402 toward the curved walls 410. For example, in FIG. 4A, a y-axis fan may be used. As another example, in FIG. 4B, an x-axis fan may be used. The fanning methods may provide various benefits for the control of the beam path 420 within the spheroid ring reflector 400.

Figure 5:
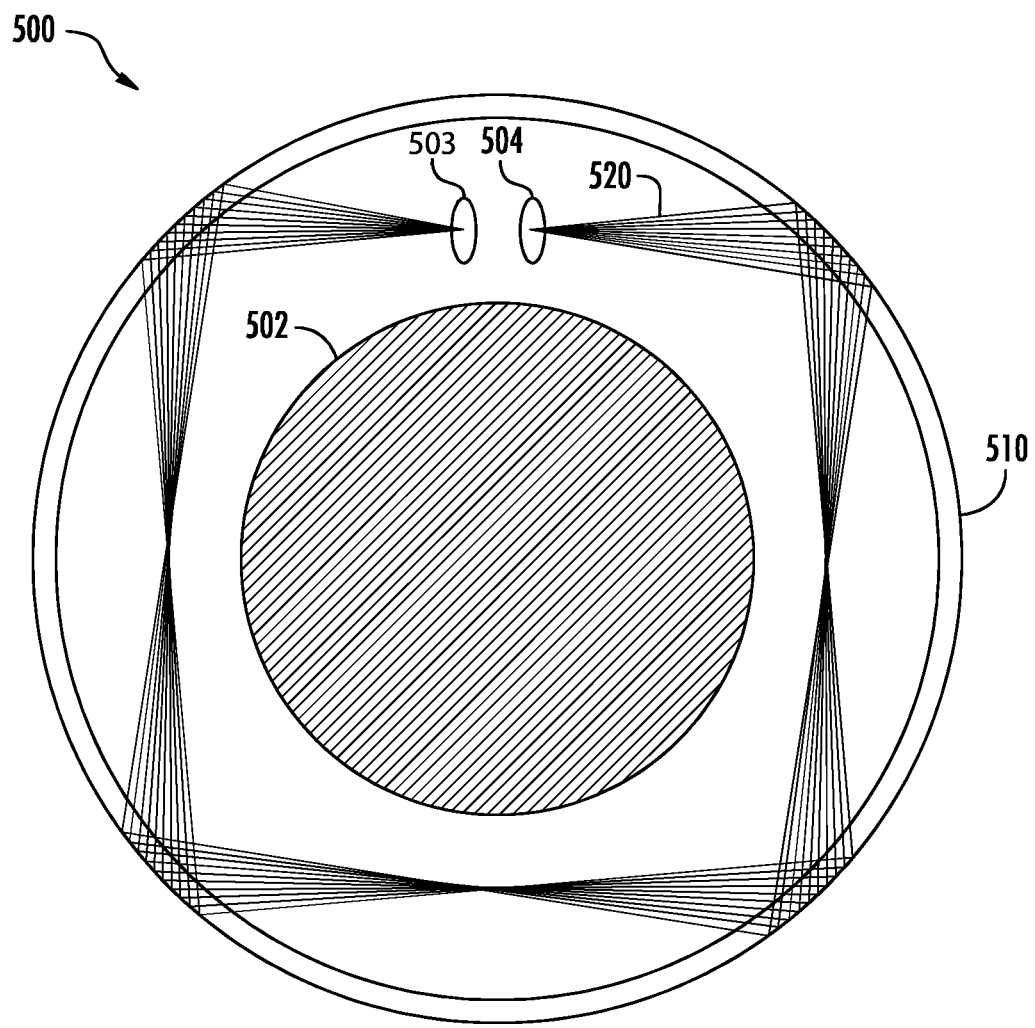
FIG. 5 illustrates a spheroid ring reflector of an integrated sensor, in accordance with an example embodiment of the present disclosure.

FIG. 5 illustrates a spheroid ring reflector 500 comprising a curved wall 510, and a central area 502 located within the center space of the spheroid ring reflector 500. The center space within the spheroid ring reflector 500 may be referred to as a "dead space" because the beam path 520 from the emitter 503 to the detector 504 does not pass through that area. The dead space is the region within the optical cavity where there is low or zero optical intensity. Therefore, when a gas is passed through the spheroid ring reflector 500, the gas that passes through the dead space may not interact with any of the beam path 520 and may be wasted. In an example embodiment, the PCBA 108 or the vertical PCB 318 of the integrated sensor 100 is extended to be positioned within the central area 502 or the dead space to incorporate the hydrogen sensor.

Figure 6:
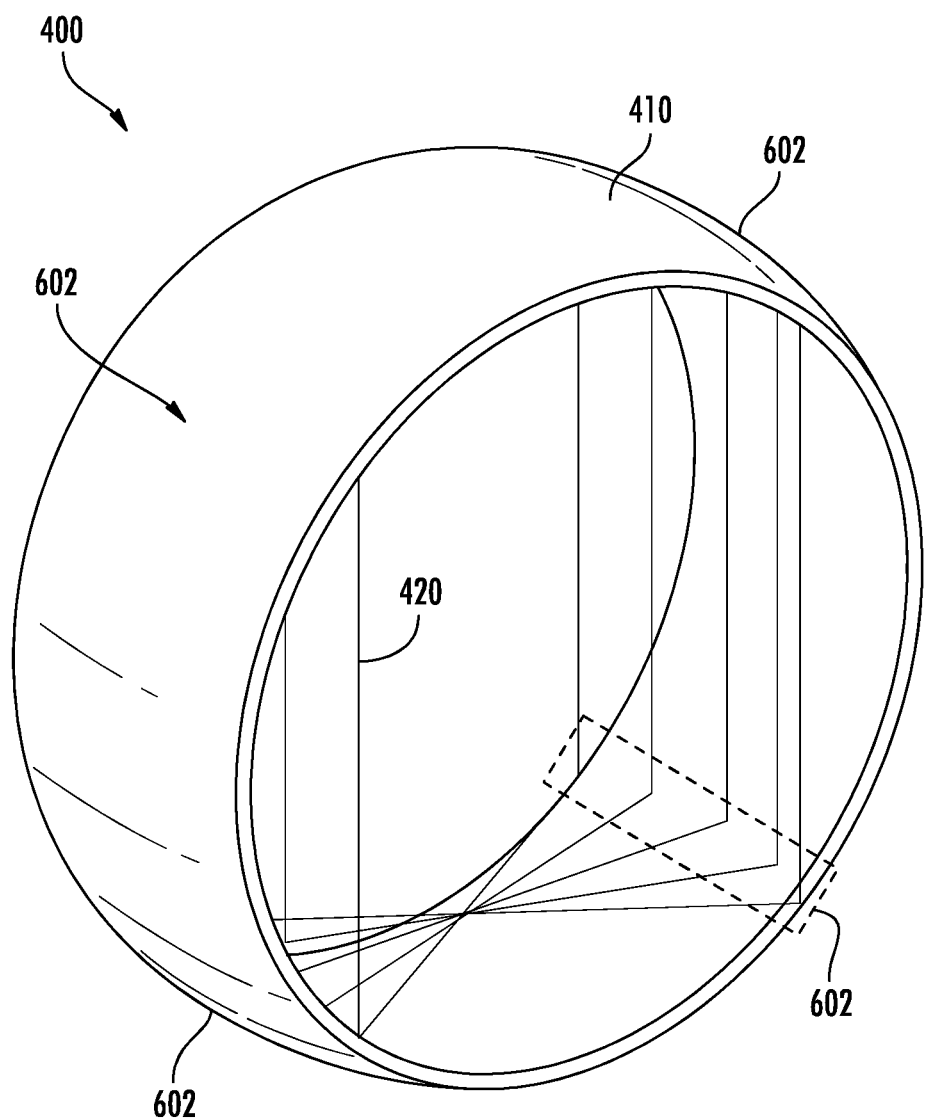
FIG. 6 illustrates radiations within a spheroid ring reflector of an integrated sensor, in accordance with an example embodiment of the present disclosure.

As shown in FIG. 6, in some embodiments, there may be certain areas 602 of the curved walls 410 where the radiation is more focused on the surface of the curved walls 410. For example, at the four corners of the beam path 420, the intensity of the radiation may be higher than in other areas of the curved walls 410. In some embodiments, the areas of the curved walls 410 that do not have a high intensity of radiation may be used for other purposes, such as locating other elements, electrical components, condensation removal elements, among other things.

Figure 7:
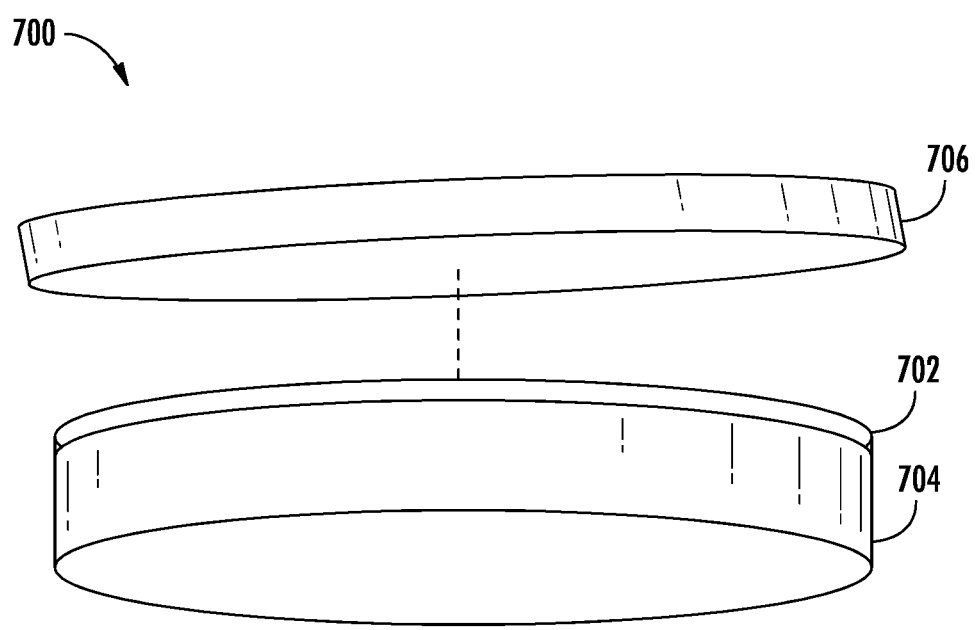
FIG. 7 illustrates a cylindrical ring of an integrated sensor, in accordance with an example embodiment of the present disclosure.

FIG. 7 illustrates a cylindrical ring 700 of the integrated sensor 100 in accordance with an example embodiment of the present disclosure. In an example, the cylindrical ring 700 is disposed in the housing 304 of the integrated sensor 100. The spheroid ring 700 has a cylindrical inner surface. The cylindrical ring 700 comprises a ring 702 and two reflective plates 704 and 706. The two reflective plates 704 and 706 are arranged on top and bottom sides of the ring 702 to reflect the light going out of the ring 702. For instance, the reflective plate 704 is positioned on bottom part of the ring 702 and the reflective plate 704 is positioned on a top portion of the ring 702. In an example, height of the cylindrical ring 700 is 1.5 mm to restrain light.

In an example, the cylindrical ring 700 can be made by resin molding. The resin molding includes molding with plastic and coating with high reflective material, such as gold, aluminum. A source and a detector with special filter are disposed in the cylindrical ring 700 for spectral absorption analysis, and the filter can be changed for various target gases such as carbon dioxide ($CO_2$), Methane ($CH_4$), Carbon Monoxide (CO), Sulfur hexafluoride ($SF_6$), Sulfur dioxide ($SO_2$), and alcohol. The method of manufacturing the cylindrical ring 700 is cost effective and increases the signal to noise ratio thereby improving the resolution of the sensor. Further, using such a cylindrical ring 700 increases average path length and total efficiency by 18.6% and 35.7%, respectively. These improvements provide enhanced sensitivity and resolution for the NDIR sensor.

Figure 8:
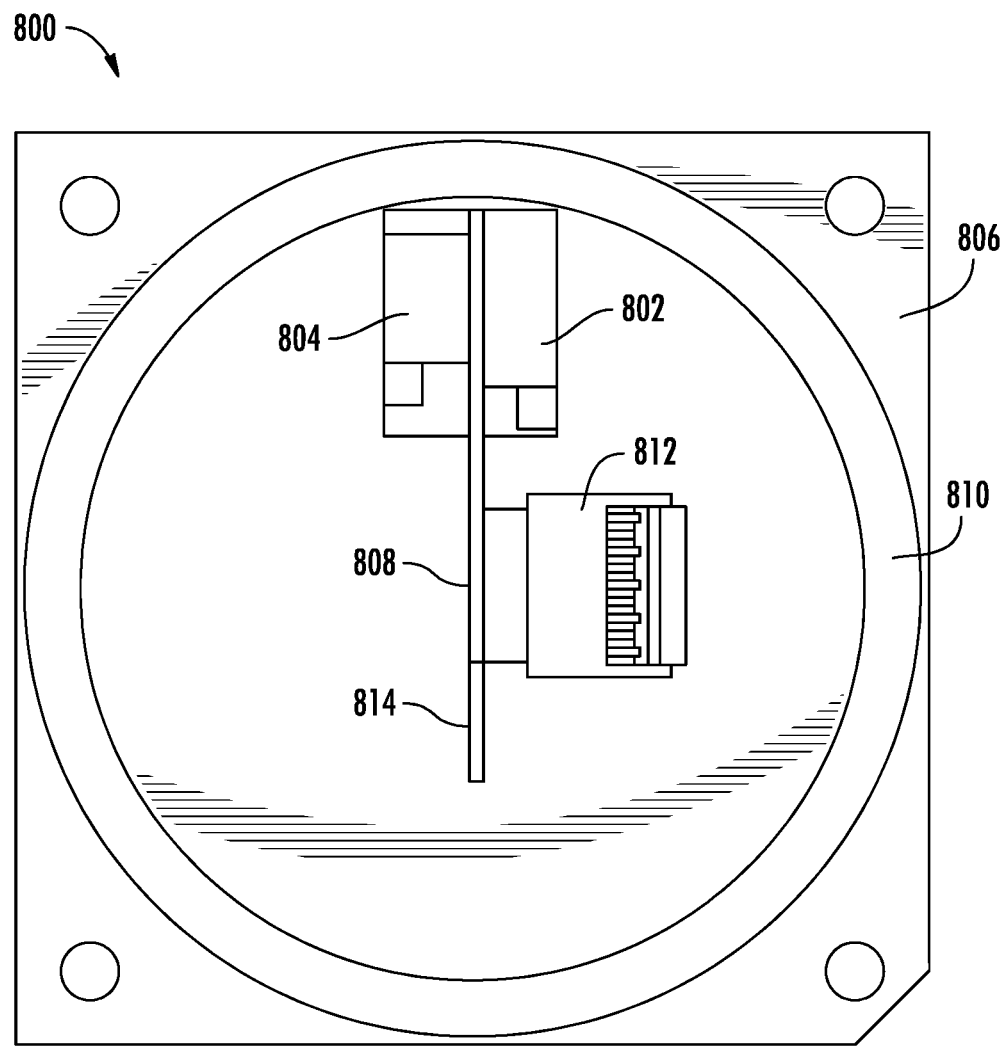
FIG. 8 illustrates a ring reflector and a printed circuit board assembly (PCBA) of a Non-dispersive Infrared (NDIR) sensor, in accordance with an example embodiment of the present disclosure.

FIG. 8 illustrate a ring reflector 800 assembled with electrical components, in accordance with an example embodiment of the present disclosure. The ring reflector 800 comprises an emitter 802, a detector 804, and a printed circuit board assembly (PCBA) 806, also referred to as PCBA 108, wherein a beam path 820 from the emitter 802 reflects off of the curved walls 810 of the ring reflector 800 toward the detector 804. FIG. 8 illustrates how the beam path 820 may generate more than one focused spot at the detector 804 due to spreading of the beam path 820. The emitter 802 and detector 804 may be attached to one or more connectors 808 and 812 configured to allow communication between the emitter 802, detector 804 and the PCBA 806. As described above, one or more of the connectors 808 and 812 may be located within the central dead space of the ring reflector 800. In an example, the PCBA 806 comprises an extended portion 814 on the vertical portion or vertical PCB 318 of the PCBA 806 disposed in the central dead space. The extended portion 814 is the additional or second gas sensor, such as the hydrogen sensor to detect presence of hydrogen in the environment. The positioning of the hydrogen sensor in the central dead space provides minimum or zero interference with the radiations that are concentrated on the peripheral region of the optical cavity. The extended portion 814 is disposed in such a manner that the hydrogen sensor is disposed in the region of the optical cavity with low or zero optical intensity such that the extended portion 814 does not impinge on critical parts of the optical path. Such a positioning of the hydrogen sensor provides uninterrupted operation of the hydrogen sensor under circumstances when the NDIR sensor is operational thereby enhancing reliability of the hydrogen sensor.

The integrated sensor 100 having a first gas sensor, such as the NDIR sensor and a second gas sensor, such as the hydrogen sensor in one package allows smaller housings and footprint of the integrated sensor 100. The integrated sensor 100 also has a low power consumption compared to pellistors and semiconductors and enables extended battery life. The integrated sensor 100 reduces design complexity and aids in accelerated product development.

It must be noted that, as used in this specification and the appended claims, the singular forms "a," "an," and "the" include plural referents unless the content clearly dictates otherwise.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments, but not other embodiments.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present disclosure are disclosed herein; however, it is to be understood that the disclosed embodiments are merely exemplary, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

While it is apparent that the illustrative embodiments herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present disclosure.

What is claimed is:

1. An integrated sensor comprising:
    a first gas sensor configured to measure a first gas, wherein the first gas sensor is an optical sensor and the optical sensor defines an optical cavity; and
    a second gas sensor configured to measure a second gas, the second gas being different from the first gas, wherein the second gas sensor is disposed within the optical cavity of the first gas sensor,
    wherein the second gas sensor is mounted within the optical cavity of the first gas sensor in a region with a low optical intensity in comparison to an optical intensity in other regions within the optical cavity.

2. The integrated sensor of claim 1, wherein the optical cavity of the first gas sensor comprises the region having the low optical intensity of radiations when the first gas sensor is operated to measure the first gas, wherein the first gas sensor comprises a Printed Circuit Board Assembly (PCBA) placed within the region of the optical cavity with the low optical intensity, and the second gas sensor mounted on the PCBA.

3. The integrated sensor of claim 1, wherein the first gas sensor is a Non-Dispersive Infrared (NDIR) sensor.

4. The integrated sensor of claim 1 further comprising a cylindrical ring in the optical cavity and two reflective plates, wherein the two reflective plates are arranged on opposite sides of the cylindrical ring.

5. A Non-Dispersive Infrared (NDIR) sensor for measuring a first gas, wherein the NDIR sensor defines an optical cavity, the NDIR sensor comprising:
    a printed circuit board assembly (PCBA) disposed within the optical cavity of the NDIR sensor, wherein the PCBA comprises:
        a gas sensor mounted on the PCBA, the gas sensor configured to measure a second gas, wherein the second gas is different from the first gas,
        wherein the gas sensor is mounted within the optical cavity of the NDIR sensor in a region with a low optical intensity in comparison to an optical intensity in other regions within the optical cavity.

6. The NDIR sensor of claim 5, wherein the gas sensor is a hydrogen gas sensor.

7. The NDIR sensor of claim 6, wherein the hydrogen gas sensor is at least one of a small solid-state electrochemical sensor or a Metal Oxide Semiconductor (MOS) sensor.

8. The NDIR sensor of claim 5, wherein the optical cavity comprises the region having the low optical intensity of radiations when the NDIR sensor is operated to measure the first gas.

9. The NDIR sensor of claim 8, wherein the PCBA is disposed within the region of the optical cavity having the low optical intensity.

10. The NDIR sensor of claim 5, wherein the optical cavity is coated with gold.

11. The NDIR sensor of claim 5 further comprising a cylindrical ring in the optical cavity and two reflective plates, wherein the two reflective plates are arranged on opposite sides of the cylindrical ring.

12. The NDIR sensor of claim 5 comprising a housing and a turret, wherein the turret is disposed on a top portion of the housing.

13. The NDIR sensor of claim 12, wherein the turret comprises a dust cover disposed on a top portion of the turret.

14. The NDIR sensor of claim 13, wherein the turret further comprises an elastomer seal positioned beneath the dust cover.

15. An integrated sensor comprising:
- a first gas sensor configured to measure a first gas, wherein the first gas sensor is an optical sensor and the optical sensor defines an optical cavity;
- a second gas sensor configured to measure a second gas, the second gas being different from the first gas, wherein the second gas sensor is disposed within the optical cavity of the first gas sensor;
- a cylindrical ring in the optical cavity of the first gas sensor; and
- two reflective plates, wherein the two reflective plates are arranged on opposite sides of the cylindrical ring.

16. The integrated sensor of claim 15, wherein the optical cavity of the first gas sensor comprises a region having a low optical intensity of radiations when the first gas sensor is operated to measure the first gas.

17. The integrated sensor of claim 16, wherein the first gas sensor comprises a Printed Circuit Board Assembly (PCBA) placed within the region of the optical cavity having a low optical intensity, and the second gas sensor mounted on the PCBA.

18. The integrated sensor of claim 15 comprising a housing and a turret, wherein the turret is disposed on a top portion of the housing.

19. The integrated sensor of claim 18, wherein the turret comprises a dust cover disposed on a top portion of the turret.

20. The integrated sensor of claim 19, wherein the turret further comprises an elastomer seal positioned beneath the dust cover.

* * * * *